(12) United States Patent
Coelingh Bennink et al.

(10) Patent No.: US 8,071,576 B2
(45) Date of Patent: Dec. 6, 2011

(54) METHOD OF PREVENTING OR TREATING BENIGN GYNAECOLOGICAL DISORDERS

(75) Inventors: Herman Jan Tijmen Coelingh Bennink, Driebergen (NL); Monique Visser, Zeist (NL)

(73) Assignee: Pantarhei Bioscience B.V. (NL)

( * ) Notice: Subject to any disclaimer, the term of this patent is extended or adjusted under 35 U.S.C. 154(b) by 1512 days.

(21) Appl. No.: 10/495,708

(22) PCT Filed: Nov. 14, 2002

(86) PCT No.: PCT/NL02/00733
§ 371 (c)(1),
(2), (4) Date: Feb. 14, 2005

(87) PCT Pub. No.: WO03/041741
PCT Pub. Date: May 22, 2003

(65) Prior Publication Data
US 2005/0148559 A1 Jul. 7, 2005

(30) Foreign Application Priority Data

Nov. 15, 2001 (EP) ..................... 01204379

(51) Int. Cl.
*A61K 31/56* (2006.01)
*A61K 31/57* (2006.01)
(52) U.S. Cl. ......... 514/170; 514/175; 514/177; 424/464
(58) Field of Classification Search .................. 514/170, 514/175, 177; 424/464
See application file for complete search history.

(56) References Cited

U.S. PATENT DOCUMENTS

| | | | | |
|---|---|---|---|---|
| 3,608,075 A | * | 9/1971 | Glen et al. | 514/182 |
| 5,340,584 A | * | 8/1994 | Spicer et al. | 424/426 |
| 5,753,639 A | | 5/1998 | Labrie | |
| 5,948,434 A | * | 9/1999 | Labrie | 424/449 |
| 6,117,446 A | * | 9/2000 | Place | 424/435 |
| 6,139,873 A | * | 10/2000 | Hughes et al. | 424/464 |
| 6,284,263 B1 | | 9/2001 | Place | |
| 2003/0004145 A1 | * | 1/2003 | Leonard | 514/170 |
| 2003/0022875 A1 | * | 1/2003 | Wilson et al. | 514/171 |

FOREIGN PATENT DOCUMENTS

WO WO 98/06404 * 2/1998
WO WO 98 06404 A 2/1998

OTHER PUBLICATIONS

Mihalyi et al., Emerging drugs in endometriosis, 2006, Expert Opinions in Emerging Drugs, 11(3), 503-524.*
Winkel, Craig A., Evaluation and Management of Women with Endometriosis, 2003, Obstertrics and Gynecologists, Elsevier, 102(2), 397-408.*
Frackiewicz et al., Diagnosis and treatment of endometriosis, 2003, Expert Opinion in Pharmacotherapy, 4(1), 67-82.*
"preventing." The American Heritage® Dictionary of the English Language, Fourth Edition. Houghton Mifflin Company, 2004. Mar. 17, 2008. <Dictionary.com http://dictionary.reference.com/browse/preventing>.*
Bergqvist A. :"Current drug therapy recommendations for the treatment of endometriosis", Drugs, vol. 58, No. 1, Jul. 1999, pp. 39-50, XP001027733, The whole document.
International Search Report—Jun. 2, 2003.

* cited by examiner

*Primary Examiner* — Mina Haghighatian
(74) *Attorney, Agent, or Firm* — The Webb Law Firm

(57) ABSTRACT

The present invention relates to a method of preventing or treating benign estrogen sensitive gynecological disorders in a female mammal, wherein the method comprises the administration to said female mammal of a combination of progestogen and androgen in an amount that is therapeutically effective to prevent or reduce the symptoms of these disorders. The present method is particularly suitable for preventing or treating disorders selected from the group consisting of endometriosis, adenomyosis, uterine fibroids, dysmenorrhoea, menorrhagia and metrorrhagia. Another aspect of the invention relates to a pharmaceutical kit comprising a plurality of oral dosage units which comprise a progestogen in an amount equivalent to 3-500 µg levonorgestrel and either 5 to 250 mg dehydroepiandrosterone or 1 to 50 mg testosterone undecanoate.

8 Claims, No Drawings

METHOD OF PREVENTING OR TREATING BENIGN GYNAECOLOGICAL DISORDERS

TECHNICAL FIELD

The present invention is concerned with a method of preventing or treating benign estrogen sensitive gynaecological disorders by administering a medicament comprising a combination of active principles, said combination including a progestogen and an androgen. More particularly the present invention is concerned with a method of preventing or treating benign estrogen sensitive gynaecological disorders, such as endometriosis, adenomyosis, uterine fibroids (leiomyomas), dysmenorrhoea, menorrhagia and metrorrhagia in female mammals, wherein the method comprises the administration of an effective amount of a combination of a progestogen and an androgen.

BACKGROUND OF THE INVENTION

Endometriosis is one of the most common gynaecological disorders, affecting 10 to 15% of women in the reproductive age. It is a benign disease defined as the presence of viable endometrial gland and stroma cells outside the uterine cavity, and is most frequently found in the pelvic area. In women developing endometriosis, these endometrial cells have the capacity to adhere to and invade the peritoneal lining, and are then able to implant and grow. It is not known yet why some women develop endometriosis and others do not. The implants respond to the menstrual cycle in a similar way as the endometrium in the uterus. However, infiltrating lesions and the blood from these lesions, unable to leave the body, cause inflammation of the surrounding tissue. The most common symptoms of endometriosis are dysmenorrhoea, dyspareunia and (chronic) abdominal pain. The occurrence of these symptoms is not related to the extent of the lesions. Some women with severe endometriosis are asymptomatic, while women with mild endometriosis may have severe pain.

Until now, no non-invasive test is available to diagnose endometriosis. Laparoscopy has to be performed to diagnose the disease. Endometriosis is classified according to the 4 stages set up by the American Fertility Society (AFS). Stage I corresponds to minimal disease while stage IV is severe, depending on the location and the extent of the endometriosis.

Endometriosis is found in up to 50% of the women with infertility. However, currently no causal relation is known to exist between mild endometriosis and infertility. Moderate to severe endometriosis can cause tubal damage and adhesions leading to infertility.

Despite extensive research, the cause of endometriosis is still largely unknown. Several theories for the origin of endometriosis have been proposed, although no single hypothesis explains all cases of the disease completely. However, the key event in all these theories is the occurrence of retrograde menstruation.

The aims of treatment of endometriosis are pain relief, resolution of the endometriotic tissue and restoration of fertility (if desired). The two common treatments are surgery or hormonal therapy or a combination of both.

Surgical treatment removes the endometriotic tissue. Initially, the pain relief using this procedure approaches 70-80%. However, the pain returns in a lot of cases because of re-growth of the endometriotic tissue. At present the most permanent way to treat endometriosis is the removal of the ovaries, thus eliminating the production of estrogens and possible other ovarian factors, which regulate the growth and activity of the endometriotic tissue.

The currently available pharmacological treatments of endometriosis are anti-inflammatory and hormonal. In the early stages of endometriosis non-steroidal anti-inflammatory drugs (NSAID's) are often successful in relieving the pelvic pain. Hormonal treatment is given mainly to downregulate the estrogen production by the ovaries. Various drugs are available for suppressing this ovarian function as will be explained below.

Danazol and gestrinone are both testosterone-derivatives, suppressing the pituitary release of follicle stimulating hormone (FSH) and luteinising hormone (LH). The efficacy of these two drugs on the regression of endometriotic tissue is no better than that of other hormonal treatments. However, both these drugs have pronounced androgenic side effects, like weight gain, acne and hirsutism, which explains the diminishing popularity of these drugs. In addition, these drugs produce a hypoestrogenic milieu.

Gonadotrophin releasing hormone (GnRH) agonists (e.g. nafareline, busereline) give a more complete suppression of the ovarian activity, leading to down-regulation of LH and FSH receptors. However, this inactivity of the ovaries does not result in disappearance of the endometriosis. Several comparative randomised studies have shown that the efficacy of these drugs is no better than that of other existing hormonal treatments. The use of GnRH agonists is limited because the women taking these drugs develop hypoestrogenic symptoms, such as hot flushes, sweating, headache, vaginal dryness, and decrease in bone mineral density (BMD). Therefore these drugs can only be administered for a maximal period of approximately 6 months. Add-back therapy (suppletion of low doses of an estrogen, an estrogen with a progestogen or a progestogen with estrogenic activity) is sometimes given to women receiving GnRH agonists, to diminish the hypoestrogenic symptoms. However, it still has to be proven if treatment with GnRH agonists and add-back therapy for more than 6 months without unwanted side effects is possible and if such a treatment remains effective against endometriosis throughout said period.

Progestogens have been used in a wide range of pharmaceutical applications for decades, including endometriosis. These drugs also work by suppressing LH and FSH and consequently induce hypoestrogenism. Examples of progestogens given for endometriosis are medroxyprogesterone acetate, dydrogesterone and lynestrenol. These drugs are also associated with side-effects e.g. mood changes and breakthrough bleedings. The treatment of endometriosis with progestogens has not received regulatory approval in the United States.

Oral contraceptives, containing both an estrogen and progestogen, are also prescribed for endometriosis. However, this treatment is not optimal, because the stimulatory effect of the estrogenic compound in the endometriotic lesions may not be counteracted effectively enough by the progestogen and because the withdrawal bleeding induced also causes bleeding in endometriotic tissue.

A large percentage of women experience relief of symptoms while being treated with the above hormonal drugs. However, symptom recurrence is likely once the drug is discontinued. None of the aforementioned drugs is suitable for long term treatment of endometriosis, because of the severe side-effects which are largely associated with hypoestrogenism. These treatments are therefore in most cases discontinued after a period of 6 months after which recurrence of the symptoms is likely to occur.

It will be evident from the above that there is a great need for a pharmaceutical treatment of endometriosis, which treatment may be applied for a longer period of time than the existing hormonal treatments, preferably until such time that the treated female reaches menopause, and/or which treatment produces better results, particularly in terms of side-effects during treatment and recurrence rate after discontinuation of the therapy. Everything that has been said above in relation to the treatment of endometriosis equally applies to other benign estrogen sensitive gynaecological disorders, notably adenomyosis, uterine fibroids, dysmenorrhoea, menorrhagia and metrorrhagia. These benign gynaecological disorders are all estrogen sensitive and treated in a comparable way as described herein before in relation to endometriosis. The available pharmaceutical treatments, however, suffer from the same major drawbacks as mentioned in connection with endometriosis, i.e. they have to be discontinued once the side-effects become more serious than the symptoms to be treated and/or symptoms reappear after discontinuation of the therapy.

SUMMARY OF THE INVENTION

The present invention relates to a method of treatment that realises the aforementioned objectives, i.e. it can be applied in the treatment of benign estrogen sensitive gynaecological disorders for a significantly longer period of time than existing medications, as it causes less side-effects and/or offers the advantage of lower recurrence rates after discontinuation than existing pharmacotherapies.

Applicants have surprisingly found that the aforementioned objectives may be realised by a method of treatment, which method comprises administration to a female mammal of a combination of a progestogen and an androgen in an amount that is therapeutically effective to prevent or reduce the symptoms of gynaecological disorders such as endometriosis, adenomyosis, uterine fibroids (leiomyomas), dysmenorrhea, menorrhagia and metrorrhagia.

The use of androgens in the treatment of benign gynaecological disorders has not been given any serious attention so far. Nonetheless, a few publications can be found in both scientific and patent literature that mention androgens in connection with e.g. endometriosis and which report on the effect of androgens on endometrium in rats.

U.S. Pat. No. 5,753,639 describes a method for treating endometriosis comprising administering at least one androgenic steroid having a Ki value for the androgen receptor of less than about $2 \times 10^{-8}$ M. Preferably said androgenic steroid is a synthetic progestin, especially medroxyprogesterone acetate.

U.S. Pat. No. 5,340,584 is concerned with methods and formulations for use in inhibiting conception and in treating benign gynecological disorders. One method disclosed in this patent comprises (a) the administration of a GnRH composition in an amount effective to suppress ovarian estrogen and progesterone production, (b) the simultaneous administration of an estrogenic composition in an amount effective to prevent symptoms of estrogen deficiency and (c) the simultaneous administration of a progestogen in an amount effective to decrease endometrial cell proliferation. It is observed in the description of the patent that in accordance with an embodiment of the invention, an androgenic composition is administered over the first period of time in conjunction with the administration of a GnRH composition, estrogenic composition and progestogen. Unlike the method of treatment described in U.S. Pat. No. 5,340,584 the present method uses progestogen rather than a GnRH analogue to suppress the endocrine ovarian function. In contrast to the method described in U.S. Pat. No. 5,340,584, the present invention provides a method for treating benign gynaecological disorders wherein the active principles can suitably be administered orally.

Sourla et al., "Effect of Dehydroepiandrosterone on Vaginal and Uterine Histomorphology in the Rat", J. Steroid Biochem. Molec. Biol. (1998), 66(3), pp. 137-149, report that following application of DHEA on the dorsal skin of ovariectomized rats the endometrium remained atrophic at all time intervals during DHEA treatment. It is concluded that the data suggest that DHEA possesses a tissue-specific action, through its local transformation into active estrogens in the vaginal epithelium while the uterine epithelium remains atrophic.

U.S. Pat. No. 6,284,263 describes buccal dosage units which comprise a progestin, an estrogen and optionally an androgenic agent, as well as a polymeric carrier that bioerodes and provides for delivery of the active agents throughout a predetermined delivery period. It is proposed in the US-patent to employ these buccal dosage units in female hormone replacement therapy, in female contraception and to treat female sexual dysfunction.

Although applicants do not wish to be bound by theory, it is believed that the surprisingly good results observed for the combination of a progestogen and an androgen are largely due to the fact that the androgen component enhances the action of the progestogen, i.e. the suppression of growth, proliferation and viability of endometriotic tissue, adenomyosis, fibroids and endometrial tissue and/or the suppression of undesirable side-effects of said progestogen, particularly those side-effects associated with hypo-androgenism.

The co-administration of an androgen together with a progestogen in accordance with the present method also helps to avoid androgen deficiency. Androgen deficiency will normally result from the prolonged administration of a progestogen (e.g. in the form of an oral contraceptive) at the dosage levels recommended in this document. The fact that the present method maintains serum concentrations testosterone in the physiological range, has a particularly advantageous effect on mood. Low serum androgen concentrations in females have been associated with feelings of discomfort. In the present method serum androgen concentrations are maintained at a level, which is sufficiently high to prevent mood changes and feelings of discomfort.

Because androgens are precursors of estrogens, one would expect administration of the androgen to enhance the growth, proliferation and viability of the endometriotic tissue, adenomyosis, fibroids and endometrial tissue, and thus to cause a worsening of the disease. However, surprisingly the androgen component used in accordance with the present invention, in contrast, has an enhancing effect on the anti-proliferative action of the progestogen on the endometrium. The androgen may exert this effect through activation of androgen receptors. It is known that androgen receptors are present in endometriotic and endometrial tissue as well as in adenomyosis. Horie et al., "Immunohistochemical localisation of androgen receptor in the human endometrium, decidua, placenta and pathological conditions of the endometrium", Hum. Repr. vol. 7, nr. 10 (1992), pp. 1461-1466 report that although the proliferation and differentiation of endometrium are mediated mainly by estrogen and progesterone receptors, the androgen receptor may play a role in modulating these changes. As yet, however, there is no scientific proof that indeed these androgen receptors play a role in the inhibition of proliferation of endometriotic tissue, adenomyosis, fibroids and endometrial tissue.

DESCRIPTION OF THE INVENTION

One aspect of the present invention is concerned with the use of a combination of active principles in the manufacture of a medicament for use in a method of preventing or treating benign estrogen sensitive gynaecological disorders in a female mammal, wherein the medicament contains a progestogen and an androgen and wherein the method comprises administration of the medicament to said female mammal so as to provide the combination of progestogen and androgen in an amount that is therapeutically effective to prevent or reduce the occurrence of these disorders, in particular by inhibiting the growth, proliferation and viability of endometriotic tissue, adenomyosis, fibroids and/or endometrial tissue. Usually the present method will achieve this goal by lowering the blood serum level of endogenous 17β-estradiol to 50 pg/ml or less, preferably to less than 30 pg/ml.

The present method preferably employs essentially no gonadotrophin releasing hormone (GnRH) analogue, meaning that if some GnRH analogue is employed, the administered amount must remain below the level where the GnRH analogue is starting to exert a physiological effect, particularly a physiological effect on the endocrine ovarian function. Most preferably the present method employs no GnRH analogue at all.

The term "androgen" as used throughout this document relates to steroids that display androgen-like activity. Although danazol and gestrinone, components used in the treatment of endometriosis, have been referred to as androgens, they are not encompassed by the term androgens as used throughout this document. The term "androgen" also does not encompass progestogens that display some androgenic activity. Examples of progestogens that display some androgenic activity are: gestodene, desogestrel and levonorgestrel. As regards the selectivity ratio of progestin-mediated effects versus androgen-mediated effects, the progestogens employed in the present method typically exhibit a selectivity ratio of at least 0.5 (reference N. B. Sobel, Progestins in preventive hormone therapy. Obstet Gynecol Clin North Am 21(1994), pp. 299-319). Androgens always display a selectivity ratio of progestin-mediated effects versus androgen-mediated effects which is well below this value.

The androgens used in the present method preferably are administered in a dosage where they exert the desired synergistic effect, but do not give rise to significant androgenic side-effects such as acne and hirsutism, as is the case for danazol and gestrinone. Preferably the androgen is administered in a dose which leads to an increase in blood serum androgen level of no more than 5 nmole total testosterone equivalent per liter, preferably less than 3 nmole total testosterone equivalent per liter and most preferably less than 1.5 nmole total testosterone equivalent per liter. The total testosterone present in the serum includes both free testosterone and bound testosterone.

In order for the present method to be effective it is desirable that the administration of the medicament, and thereby the administration of the progestogen and androgen, occurs in an amount which is therapeutically effective to suppress the endocrine ovarian function. Effective suppression of the endocrine ovarian function means that estrogen serum concentrations (notably 17β-estradiol-levels) and consequently endogenous progesterone serum concentrations will be suppressed to such a level that virtually no growth of endometrial tissue will occur. When the ovaria are sufficiently suppressed, this will normally induce amenorrhoea. Preferably the combination of the progestogen and androgen is provided in an amount that is therapeutically effective to inhibit endometrial growth.

The medicament used in the present method may be administered in ways that are well known in the pharmaceutical art. It was found, however, that oral, percutaneous, and intravaginal administration of the medicament are most effective. Oral administration is a particularly preferred mode of administration as it was found to be both effective and very user-friendly.

The present method may successfully be applied to female mammals. Preferably these mammals include humans, cattle and pets. Most preferably the female mammal is a human female.

The main function of the progestogen as used in the present method is to reduce growth and proliferation of endometriotic tissue, adenomyosis, fibroids and/or endometrial tissue by suppressing the secretion of estrogen through inhibition of the pituitary release of FSH and LH. An unexpected advantage of the present method is the observation that the negative mood effects and vaginal dryness normally associated with the administration of progestogens is significantly improved by the co-administration of an androgen.

The progestogen used in the present method may suitably be selected from the group consisting of levonorgestrel, norgestimate, norethisterone, dydrogesterone, drospirenone, 3-beta-hydroxydesogestrel, etonogestrel (=3-keto desogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime, precursors of these compounds capable of liberating such a progestogen when used in the present method and mixtures thereof.

In a preferred embodiment the progestogen is selected from the group consisting of levonorgestrel, norgestimate, norethisterone, drospirenone, dydrogesterone, trimegestone, dienogest, precursors of these progestogens and mixtures thereof.

Specific examples of progestogen precursors which may be employed in accordance with the present invention include: anagestone acetate, chlormadinone acetate, cyproterone acetate, gestodene acetate, hydroxymethylprogesterone acetate, hydroxyprogesterone acetate, hydroxyprogesterone hexanoate, hydroxyprogesterone caproate, hydroxyprogesterone enanthate, medroxyprogesterone acetate, megestrol acetate, melengestrol acetate, nomegestrol acetate, norethindrone acetate, norethisterone acetate, norethisterone enanthate, quingestanol acetate, (17alpha)-17-hydroxy-11-methylene-19-norpregna-4,15-diene-20-yn-3-one, tibolone, algestone acetophenide, nestorone, promegestone, 17-hydroxyprogesterone esters, 19-nor-17hydroxyprogesterone esters, 17alpha-ethinyl-testosterone.

As mentioned before, the present method preferably employs essentially no GnRH analogues, i.e. GnRH agonists and/or GnRH antagonists. Examples of GnRH agonists are: nafarelin, buserelin, leuprolin, goserelin, triptorelin, deslorelin, avorelin, histrelin. Examples of GnRH antagonists include: cetrorelix, ganirelix, abarelix, iturelix, prazarelix, antarelix, ORG 30850, HOE 2013, A-75998, A-76154, A-222509, A-198401, A-84861, Nal-Glu, D-63153, FE-200486.

The present method may suitably be used for the treatment of a variety of benign estrogen sensitive gynaecological disorders. Such disorders include endometriosis, adenomyosis, uterine fibroids, dysmenorrhea, menorrhagia and metrorrhagia The present method is particularly effective when used in the treatment of endometriosis and adenomyosis, as the main symptoms of these disorders are directly related to endometrial proliferation. Most preferably the present method is used in the treatment of endometriosis.

The androgen used in the present method is preferably selected from the group consisting of dehydroepiandrosterone (DHEA); DHEA-sulphate (DHEAS); testosterone; testosterone esters such as testosterone undecanoate, testosterone propionate, testosterone phenylpropionate, testosterone isohexanoate, testosterone enantate, testosterone bucanate, testosterone decanoate, testosterone buciclate; methyltestosterone; mesterolon; stanozolol; androstenedione; dihydrotestosterone; androstanediol; metenolon; fluoxymesterone; oxymesterone; methandrostenolol; MENT, precursors capable of liberating these androgens when used in the present method and mixtures thereof. Most preferably the androgen is selected from the group consisting of DHEA, pharmaceutically acceptable testosterone esters such as testosterone undecanoate, androstenedione, precursors capable of liberating these androgens when used in the present method and mixtures thereof. Preferably the testosterone esters employed in the present method comprise an acyl group which comprises at least 6, more preferably from 8-20 and preferably 9-13 carbon atoms. Most preferably the androgen used in the present method is DHEA and/or testosterone undecanoate. These androgens offer the advantage that they can effectively be used in oral dosage units.

In a preferred embodiment the androgen is provided in an amount equivalent to a daily oral dosage of 5 to 250 mg DHEA, which is equivalent to a daily oral dosage of 1 to 50 mg testosterone undecanoate. More preferably the androgen is provided in an amount equivalent to a daily oral dosage of 20 to 100 mg DHEA, most preferably in an amount equivalent to a daily oral dosage of 40 to 60 mg DHEA. The phrase "equivalent to a daily dosage" should not be interpreted restrictedly. For instance, the above mentioned requirement that the administration of the present medicament is to provide the equivalent of a daily dosage of 5 to 250 mg DHEA, encompasses a protocol wherein DHEA is administered once a week, provided the weekly dosage is between 35 and 1750 mg, i.e. such that the average daily dose is between 5 and 250 mg DHEA.

The androgen used in accordance with the present invention, preferably is not an androgenic synthetic progestin as described in U.S. Pat. No. 5,753,639.

It is noted that, for instance, DHEA, testosterone undecanoate and androstenedione are precursors of testosterone and that said precursors per se exhibit virtually no affinity for the androgen receptors in the female body. The effectiveness of androgens within the method of the invention is determined by their functionally active form, which may well be different from the form in which they are administered.

DHEA and its sulphate ester (DHEAS) are the major secretory products of the human adrenal gland and collectively circulate at levels far exceeding any other steroid in the body. DHEA is a precursor for the androgen testosterone and for the estrogenic hormones estrone and estradiol. Once DHEA is released into the body from the adrenal gland it is partly converted into the sulphate ester DHEA-S by the liver. Many tissues are able to convert DHEAS back to DHEA, which in turn can act as a precursor for testosterone, estrone and estradiol. The liver and the kidney are the principal organs involved in clearing steroid hormones from the circulation. Hepatic metabolism accomplishes two functions for DHEA: a decrease in the biologic activity of the hormone, and an increase in its water solubility, because of conversion to the hydrophilic sulphate form that can be excreted in urine.

In order to obtain the desired impact from the present method it is advisable to administer the medicament at a dosage sufficient to maintain serum androgen concentration of the female mammal within a (physiological) range which is equivalent to between 0.5 and 5.0, preferably to between 0.7 and 4.0, most preferably between 1.0 and 3.0 nanomoles total testosterone per liter. Again, these testosterone concentrations include both free and bound testosterone.

In accordance with the method of the invention the medicament may be administered at intervals which may range from 6 hours to 2 weeks. Preferably however, the medicament is administered at least once daily as this helps to minimise fluctuations in blood serum levels of the active principles. Most preferably the medicament is administered once daily. In case the medicament is administered once daily, it is advantageous to administer the medicament in the morning, particularly between 6:00 a.m. and 10:00 a.m. By administering the medicament in the morning the serum concentration of the androgen will follow an almost natural pattern, which is believed to have an advantageous effect on e.g. mood.

In a particularly preferred embodiment of the invention, the method comprises continuous administration of the medicament for a period of at least 3 months, preferably at least 6 months, so as to provide the combination of the progestogen and androgen in an amount that is therapeutically effective to suppress endocrine ovarian function during said period.

The term "continuous" when used in relation to the administration of one or more active principles, means that said one or more active principles are administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, an administration regimen is deemed to be continuous if the longest interval between 2 subsequent administrations is not more than 3.5 times as long as the average interval. Even more preferably said longest interval is not more than 2.5 times as long as the average interval.

The combination of active principles used in the present method may advantageously also comprise an estrogen. The present method, in the absence of co-administered estrogen, will inevitably lead to a lowering of the endogenous estrogen (17β-estradiol) levels in the female body. This lowering of blood serum estrogen levels will increase the risk of hypoestrogenism. Hypoestrogenism is associated with a range of undesirable symptoms such as hot flushes, vaginal dryness, osteoporosis etc. In order to prevent or suppress these symptoms it was found advantageous for the combination of active principles to additionally include an estrogen in a therapeutically effective amount to reduce or prevent symptoms of hypoestrogenism.

The estrogen used in the present method is preferably selected from the group consisting of ethinyl estradiol, mestranol, quinestranol, estradiol, estrone, estran, estriol, conjugated equine estrogens, precursors capable of liberating such an estrogen when used in the present method and mixtures thereof In a preferred embodiment of the method of the invention the estrogen is selected from the group consisting of ethinyl estradiol, estradiol, precursors of these estrogens and mixtures thereof Preferably, in the present method, the estrogen is administered in an amount equivalent to a daily oral dosage of 1-40 µg ethinyl estradiol (e.g. 0.5-5 mg 17β-estradiol).

It is to be understood that the present invention not only encompasses the use of the androgens, progestogens and estrogens specifically mentioned in this application, but also metabolites of these active principles that display comparable functionality in the present method. In this context it is noted that, for instance, levonorgestrel is a metabolite of norgestimate, that estriol is a metabolite of 17β-estradiol and that testosterone is a metabolite of DHEA. All these steroids have found application in contraceptive formulations and/or preparations for hormone replacement therapy.

In another especially preferred embodiment of the invention the method of treatment comprises 2 phases, a first phase of at least 30 days and at most 120 days, preferably at least 60 days and at most 90 days, during which a progestogen and no estrogen is provided, optionally in the absence of an androgen, in an amount that is effective to suppress the endocrine ovarian function, and a second phase of at least 3 months during which the combination of a progestogen, estrogen and androgen is provided in a daily amount effective to suppress endocrine ovarian function. It is a well-known fact that therapies such as the present method are often discontinued because women undergoing such therapy suffer from vaginal spotting and unexpected bleeding. The 2-phase method ensures that bleeding in the form of spotting and unexpected bleeding is minimised throughout the treatment, including the initial phase.

Because the incidence of the aforementioned benign gynaecological disorders drops sharply after females have reached menopause, the present method is particularly useful when used in the treatment of pre-menopausal females.

A suitable dose of the progestogen may be readily identified by determining the lowest dose of the combination of progestogen and androgen that is sufficient to reduce the endogenous 17β-estradiol blood serum level of the female, within a period of 14 days, to less than 50 pg/ml, preferably even less than 30 pg/ml. With reference to the exemplary progestogen levonorgestrel this dose would usually be in the range of 30 to 500 µg per day, preferably of 50 to 400 µg per day and most preferably 100 to 300 µg per day. As will be readily understood by those working in the field, the amount of progestogen and androgen effective to achieve the desired results may be determined empirically with respect to any given progestogen and androgen and for any given mammal. The effective dose ranges, as well as being compound specific, may also depend upon patient characteristics, such as age and weight. Further, the effective amount of the active principles also depends upon the route of administration.

Another aspect of the present invention relates to a pharmaceutical kit comprising a plurality of oral dosage units which comprise a progestogen in an amount equivalent to 30-500 µg levonorgestrel and 5 to 250 mg dehydroepiandrosterone and/or 1 to 50 mg testosterone undecanoate. Typically, the oral dosage units contain either dehydroepiandrosterone or testosterone undecanoate. Preferably all the dosage units within the kit comprise the combination of a progestogen and dehydroepiandrosterone or of a progestogen and testosterone undecanoate. The kit may suitably comprise at least 10, more preferably at least 60 oral dosage units. The dosage units may be in the form of e.g. tablets or capsules.

In a particularly preferred embodiment, the oral dosage units within the present kit contain dehydroepiandrosterone in an amount of at least 15 mg, more preferably of at least 20 mg, most preferably of at least 40 mg. Testosterone undecanoate is preferably contained in the present dosage units in an amount of at least 3 mg, more preferably ot at least 4 mg, most preferably of at least 8 mg. The amount of dehydroepiandrosterone in the dosage units preferably does not exceed 100 mg, more preferably it does not exceed 80 mg, most preferably it does not exceed 60 mg. The amount of testosterone undecanoate in the dosage units preferably does not exceed 20 mg, more preferably it does not exceed 16 mg, most preferably it does not exceed 12 mg.

In a preferred embodiment the present pharmaceutical kit comprises a plurality of oral dosage units comprising a progestogen in an amount equivalent to 50-400 µg, preferably 100-300 µg levonorgestrel and 20 to 100 mg, preferably 40 to 60 mg dehydroepiandrosterone.

In yet another preferred embodiment the aforementioned plurality of oral dosage units additionally contain an estrogen in an amount equivalent to 1 to 40 µg ethinyl estradiol.

Preferably said estrogen is selected from the group consisting of ethinyl estradiol and 17β-estradiol. Most preferably the estrogen is ethinyl estradiol.

The invention is further illustrated by means of the following examples.

EXAMPLES

Example 1

The effects on endometrium of the progestogen levonorgestrel and the androgen testosterone were determined in rabbits according to the method of McPhail (Mc Phail M. K. "The assay of progestin" J Physiol (1934), 83, 145-156). Four groups of each 5 rabbits were pretreated with daily subcutaneous dosages of 5 µg 17β-estradiol for 6 days.

After pretreatment, 3 groups either received levonorgestrel at an oral dose of 8 µg per day for 5 days, testosterone in a subcutaneous dose of 20 mg per day for 5 days, or levonorgestrel and testosterone together in the aforementioned routes and doses for 5 days. The fourth group was used as the negative control.

Autopsy was performed after the treatment period and the uterus was weighed and histological sections were prepared from each uterine horn and these were microscopically evaluated according to the McPhail Index (scores 0-4; 0=no differentiation; 4=maximal differentiation).

The pre-treatment phase induced proliferation of the endometrium. In the second phase, when the study compounds were administered, the degree of endometrial differentiation (transformation) was investigated. The levonorgestrel group showed a McPhail index of 2.1±0.4, while the testosterone only group had a McPhail index of 2.9±0.1. When levonorgestrel and testosterone were given together a McPhail index of 3.7±0.2 was observed. Thus, significantly more differentiation of the endometrium was observed when levonorgestrel and testosterone were given together compared to the groups only receiving levonorgestrel or testosterone, indicating that progestogen and androgen have an additive transforming effect on endometrial tissue. No further proliferation of the endometrium was observed in any of the treatment groups in the second phase of the McPhail study.

This reflects the anti-proliferative effect of progestogen and androgen on endometrial tissue. In this setting it was presumed that the effect of the study compounds on the endometrial tissue is indicative of the effect on endometriotic tissue. This is a reasonable presumption because this latter tissue is essentially identical to endometrial tissue.

Example 2

A clinical study is conducted in 200 healthy young women. Four groups of 50 women, who use a combined oral contraceptive containing at least 30 microgram ethinyl estradiol for at least 19 days before the start of the study, receive a daily oral dose of 20 microgram ethinyl estradiol and 100 microgram levonorgestrel, or 30 microgram ethinyl estradiol and 150 microgram levonorgestrel, either with or without 50 mg DHEA for 104 days (15 weeks) without pauses. Vaginal spotting and bleeding is scored daily by the participants in a diary and the effects on general well being are scored at baseline and at each study visit (every 5 weeks during study drug administration) on a psychometric rating scale. The psychometric rating scale used is especially suited for identifying differences in a population of healthy young women. The scale is a 24-item (placid, sleepy, jittery, intense, lacking confidence, energetic, sensitive, tired, well-balanced, at-rest, drowsy, fearful, lively, sickly, in a good mood, irritable, lethargic, quiet, full-of-pep, optimistic, moody, active, tense, sad), 4-point (yes, definitely; yes, a bit; no, in fact not; no, definitely not) scale to be scored by the woman herself. In addition, endocrine measurements are performed in a subgroup of the participants (17β-estradiol, progesterone, total testosterone, LH, FSH and SHBG).

Results show that in the groups of women receiving DHEA less vaginal breakthrough spotting and bleeding is reported and generally better scores are obtained on items in the domain of energy (viz. tired, drowsy, energetic, placid and lethargic) and less side effects occur than in those women not receiving it. In addition, in the participants receiving DHEA significantly higher testosterone levels are seen which are well within the physiological range.

Example 3

A clinical study is conducted in 100 healthy young women. Two groups of 50 women, who use a combined oral contraceptive containing at least 30 microgram ethinyl estradiol for at least 19 days before the start of the study, receive a daily oral dose of 3 mg 17β-estradiol and 1.5 mg norethisterone acetate either with or without 50 mg DHEA for 104 days (15 weeks) without pauses. Vaginal spotting and bleeding is scored daily by the participants in a diary. The effects on general well being are scored at baseline and at each study visit (every 5 weeks during study drug administration) using the psychometric rating scale described in example 2.

Ovulation inhibition is investigated by analysing pregnanediol samples twice a week during 4 weeks between week 7 and 14. In addition, endocrine measurements are performed in a subgroup of the participants (17β-estradiol, progesterone, total testosterone, LH, FSH and SHBG).

Again results show that in the groups of women receiving DHEA less vaginal breakthrough spotting and bleeding is reported and generally better scores are seen on items in the domain of energy (viz. tired, drowsy, energetic, placid and lethargic) and less side effects occur than in those women not receiving it. In addition, in the participants receiving DHEA significantly higher testosterone levels are seen which are well within the physiological range. Although the number of participants is small, both regimens appear to suppress ovulation consistently.

The invention claimed is:

1. A method of treating a benign estrogen sensitive gynaecological disorder in a female mammal, said benign estrogen sensitive gynaecological disorder being selected from the group consisting of endometriosis, adenomyosis, uterine fibroids and dysmenorrheal; and said method comprising once daily orally administering to said female mammal a dosage unit comprising a combination of progestogen, ethinyl estradiol and dehydroepiandrosterone (DHEA) in an amount that is therapeutically effective to reduce the symptoms of said disorder, the progestogen being selected from the group consisting of levonorgestrel, norgestimate, norethisterone, drospirenone, dydrogesterone, trimegestone, dienogest, precursors thereof and mixtures thereof and being contained in said dosage unit in an amount equivalent to 30 to 500 µg levonorgestrel; the ethinyl estradiol being contained in said dosage unit in an amount of to 1 to 40 µg; and DHEA being contained in said dosage unit in an amount of 20 to 100 mg.

2. The method according to claim 1, wherein the combination of the progestogen and androgen is provided in an amount that is therapeutically effective to suppress endocrine ovarian function.

3. The method according to claim 1, wherein the combination of active principles additionally comprises an estrogen in a therapeutically effective amount to reduce symptoms of hypoestrogenism.

4. The method according to claim 1, wherein the method comprises oral administration of the dosage unit.

5. The method according to claim 1, wherein the benign estrogen sensitive gynaecological disorder is selected from the group consisting of endometriosis and adenomyosis.

6. The method according to claim 1, wherein the combination of progestogen and androgen is administered in an amount that is sufficient to reduce the endogenous 17β-estradiol blood serum level of the female, within a period of 14 days, to less than 50 pg/ml.

7. The method according to claim 1, wherein the dosage unit is administered at a dosage sufficient to maintain serum androgen concentration of the female mammal at a level equivalent to between 0.5 and 5.0 nanomoles total testosterone per liter.

8. The method according to claim 1, wherein the method comprises continuous administration of the dosage unit for a period of at least 3 months so as to provide the combination of progestogen and androgen in an amount that is therapeutically effective to suppress ovarian function during said period.

* * * * *